United States Patent
Micheels et al.

(10) Patent No.: US 7,840,360 B1
(45) Date of Patent: Nov. 23, 2010

(54) OPTICAL SYSTEM AND METHOD FOR INSPECTION AND CHARACTERIZATION OF LIQUIDS IN VESSELS

(76) Inventors: Ronald H. Micheels, c/o Polestar Technologies, Inc., 220 Reservoir St., Suite 32, Needham Heights, MA (US) 02494; Ranganathan Shashidhar, c/o Polestar Technologies, Inc., 1940 Duke St., Suite 215, Alexandria, VA (US) 22314; Karen K. Carpenter, c/o Polestar Technologies, Inc., 220 Reservoir St., Suite 32, Needham Heights, MA (US) 02494

( * ) Notice: Subject to any disclaimer, the term of this patent is extended or adjusted under 35 U.S.C. 154(b) by 333 days.

(21) Appl. No.: 11/977,873

(22) Filed: Oct. 26, 2007

Related U.S. Application Data

(60) Provisional application No. 60/854,602, filed on Oct. 26, 2006.

(51) Int. Cl.
*G01J 5/00* (2006.01)
*G01N 37/00* (2006.01)

(52) U.S. Cl. .................. 702/25; 250/223 B; 250/338.1; 250/339.06; 382/142; 73/61.43

(58) Field of Classification Search .................. 702/25; 250/338.1, 339.06, 223 B; 73/61.43; 382/142
See application file for complete search history.

(56) References Cited

U.S. PATENT DOCUMENTS

| | | | |
|---|---|---|---|
| 5,536,935 A | 7/1996 | Klotzsch et al. | |
| 5,754,297 A * | 5/1998 | Nulman | 356/630 |
| 6,545,278 B1 | 4/2003 | Mottier et al. | |
| 6,661,909 B2 | 12/2003 | Youvan et al. | |
| 6,753,527 B1 * | 6/2004 | Yamagishi et al. | 250/339.06 |
| 7,033,070 B2 * | 4/2006 | Azami | 374/131 |
| 7,255,835 B2 * | 8/2007 | Franzen et al. | 422/82.11 |
| 2004/0159789 A1 | 8/2004 | Treado et al. | |
| 2005/0012928 A1 * | 1/2005 | Sezginer et al. | 356/401 |
| 2006/0197947 A1 | 9/2006 | Wang et al. | |

OTHER PUBLICATIONS

International Search Report in corresponding International Appl. No. PCT/US07/22656.

\* cited by examiner

*Primary Examiner*—Hal D Wachsman
*Assistant Examiner*—Janet L Suglo
(74) *Attorney, Agent, or Firm*—Townsend & Banta

(57) ABSTRACT

A system and method for non-invasively inspecting one or more vessels capable of transmitting IR light containing liquid is provided, which uses a near-infrared (NIR) imaging device in combination with one or two NIR light sources, a diffuser plate, and an optical wavelength selecting means is provided for selecting one or more wavelength bands. In addition, the system may further comprise a computer processing means, a computer database containing known absorbance values, and a computer application, such that the system may compare the collected spectroscopic data to known spectroscopic data, and identify the liquid contained within the inspected vessel. The inspection method of the present invention measures a transmission or reflection image of one or more vessels being inspected at one or more narrow wavelength intervals in the NIR spectral range that corresponds to a peak absorbance wavelength of water, organic liquids, and explosive compositions.

8 Claims, 14 Drawing Sheets
(7 of 14 Drawing Sheet(s) Filed in Color)

OPTICAL SYSTEM AND METHOD FOR INSPECTION AND CHARACTERIZATION OF LIQUIDS IN VESSELS

This application is a corresponding application of pending U.S. provisional application Ser. No. 60/854,602, filed Oct. 26, 2006, which is incorporated herein by reference.

FIELD OF THE INVENTION

An optical imaging system, and a method utilizing same, is provided, for security inspection of bottles or other containers of liquids for hazardous and contraband liquids in, for example, airports, building and stadium entrances, military and government facility checkpoints, customs checkpoints. In particular, a system utilizing near-infrared spectral image characterization is provided for non-invasively characterizing the liquid contents of vessels (such as bottles or other transparent or semi-transparent containers capable of transmitting near-infrared (NIR) light), using analysis of transmitted or reflected light in the NIR range, to determine if the liquid contents are hazardous or contraband materials, by determining whether they are water-based or organic liquid-based.

BACKGROUND OF THE INVENTION

The emergence of global terrorist threats and a marked increase in the smuggling of contraband has created the need for systems and methods to detect explosives, flammable liquids, chemical warfare agents, and illegal or controlled drugs in public locations. For example, security personnel in locations such as airports, building and stadium entrances, military and government facility checkpoints, and customs checkpoints must now have the ability to quickly and accurately scan items and persons, and determine whether any of the above described contraband is present. Currently, various invasive and non-invasive systems and methods are employed, but none of these conventional systems and techniques is capable of accurately distinguishing water-based liquids from organic liquids in a variety of liquid containers.

For example, ultrasonic reflection techniques at one or more ultrasonic frequencies are used to characterize liquids, to some degree, by analyzing the speed of sound travel through, and heat capacity of, liquids under inspection. Such ultrasonic reflection techniques measure such parameters as ultrasonic velocity, attenuation, reflection coefficients, and scattering amplitudes, which are related to fundamental physical properties of fluids and slurries of interest to food processors and manufacturers of consumer products. Non-invasive ultrasonic methodologies have been developed that offer on-line, real-time analysis of many physical properties, including fluid viscosity, density, sheer rate, particle size distribution, concentration, settling and plug formation, fouling and pipeline wall buildup detection, liquid-liquid interface detection, and some low specificity chemical identity confirmation. Many of the ultrasonic reflection methodologies mentioned above have developed into practical monitoring devices.

Conventional ultrasonic instrumentation (measuring) devices, as discussed above, are well-established performers in a myriad of industrial applications. Several new ultrasonic systems with applications to the food industry have been developed, including an ultrasonic rheometer, an ultrasonic densimeter, and an ultrasonic liquid characterization device. These ultrasonic systems were initially developed in response to environmental and national needs to non-invasively measure the physical properties of liquids and slurries.

U.S. Pat. No. 5,767,407 describes a method for rapid, non-invasive identification and monitoring of chemicals in sealed containers or containers, where direct access to the chemical is not possible. Multiple ultrasonic acoustic properties (up to four) of a fluid are simultaneously determined. The method described in U.S. Pat. No. 5,767,407 can be used to provide some chemical identification information, and for determining changes in known chemicals from a variety of sources. However, the method described therein does not provide for identification of all known chemicals, only those identifiable based on certain measured parameters, and only known classes of chemicals in suspected containers, such as in chemical munitions, can be characterized. In addition, a significant number of industrial chemicals can be identified.

However, ultrasonic sensing is not very selective, and can only differentiate liquids by properties such as viscosity, and the speed of sound, which can result in ambiguity in distinguishing certain organic liquids from water. Furthermore, the presence of particulates, such as those present in baby formula, can interfere with the sensing process. In addition, when using the ultrasonic sensing approaches described above, problems may be encountered with containers having irregular shapes, or having a small radius of curvature which would not interface well with a flat or fixed geometry probe transducer surface. Conventional ultrasonic reflection techniques have been found to be not as selective as near-infrared spectral characterization techniques at one or two near-infrared wavelengths, and are not capable of quickly and accurately distinguishing water-based liquids from organic compound-based liquids, as required in security applications.

Similar to ultrasonic liquid inspection is electromagnetic radio or microwave frequency dielectric constant monitoring devices, which measure differences in dielectric constants. Dielectric constants vary between different liquids, but will not necessarily be unique for every liquid of interest. Like ultrasonic techniques, dielectric sensing is not highly specific to molecular structure, and occasionally fails to distinguish certain organic liquids from water. Also, thick bottle or container walls can interfere with the accuracy of dielectric sensing. Further, dielectric sensing techniques sometimes encounter problems when analyzing containers having irregular shapes or a small radius of curvature, which does not interface well with a flat probe transducer surface.

Another conventional technique used to identify compositions is Laser-Raman spectroscopy. This technique can be used for selective chemical identification of liquids contained inside of clear containers, but has difficulty when inspecting containers with pigments in the walls of said containers, or in penetrating labels on the containers, if the pigments in the container walls or labels are strongly absorbing, scattering or fluorescent at the laser wavelength (which is usually about 785 nm). Specifically, pigments contained in the bottle or container wall, or in labels and paper in labels, can interfere through light scattering or optical absorption of the laser light, which is typically at 785 nanometers (nm) for lower cost and portable laser-Raman systems, or by fluorescence induced by the laser. Further, Laser-Raman spectroscopy involves expensive instrumentation which can be temperature and vibration sensitive.

A further conventional inspection technique is X-ray fluorescence spectroscopy. This technique can provide elemental analysis information about a liquid contained inside of a bottle. However, X-ray fluorescence only determines the atomic composition, and is not sensitive to elements with atomic numbers less than sodium (Na). The X-ray fluorescence emission corresponding to elements lighter than Na is absorbed by small path lengths (i.e. 2 mm) through air, and requires the sample be placed in a vacuum container to be detected. As such, X-ray fluorescence cannot be used to detect hydrogen, oxygen, nitrogen, or carbon, all of which must be detected to differentiate water from organic liquids in general.

In view of the deficiencies of the conventional inspection techniques, as discussed above, it is an object of the provide a system and method capable of detecting and distinguishing organic from aqueous liquids, disposed inside of vessels capable of transmitting NIR light.

It is another object of the present invention to provide a system and method to distinguish organic from aqueous liquids inside of such vessels with enhanced contrast and reduced interference from labels disposed on the vessels.

It is yet another object of the present invention to provide a system and method to distinguish organic from aqueous liquids for liquids in such vessels containing substantial concentrations of particulates or emulsions.

It is another object of the present invention to provide a system and method to detect the presence of an organic or other hazardous liquid present in a smaller vessel that is concealed within a larger vessel that holds an aqueous liquid.

It is another object of the present invention to provide a system and method to simultaneously inspect groups of two or more vessels, so as to be capable of detecting the presence of a hazardous liquid in one or more of the vessels.

It is yet another object of the present invention to distinguish organic from aqueous liquids for liquids in vessels containing substantial concentrations of particulates or emulsions, by differential wavelength NIR reflectance imaging (between 980 nm and 1050 nm, 980 nm and 920 nm, or other pairs of wavelengths corresponding to peak water absorptions and adjacent off-peak wavelengths). Differential wavelength imaging, involving the technique of subtracting an image of an object measured at a first wavelength band from an image measured at a second wavelength band, where the position of the object relative to the camera is the same for both image measurements, enables same.

It is another object of the present invention to detect the presence of an organic or other hazardous liquid present in a smaller vessel that is concealed within a larger vessel that holds an aqueous liquid, using single or differential wavelength NIR transmission or reflectance imaging. In addition to the wavelengths of 920, 980, and 1050, other wavelengths may be used for the NIR image detection of vessels of organic liquids concealed within larger vessels holding aqueous liquids.

It is another object of the present invention to provide an imaging system and method to inspect one or more vessels capable of transmitting NIR light, determine the peak absorbances of the light transmitted or reflected therefrom, compare the measured peak absorbances to a database of known absorbances of liquid explosives, and determine whether a known liquid explosive is contained in the vessel, and what liquid explosive it is.

SUMMARY OF THE INVENTION

In order to achieve the objects of the present invention, as discussed above, the present inventors earnestly endeavored to develop a system and method capable of non-invasively inspecting the contents of vessels capable of transmitting NIR light (such as bottles, cardboard containers or paper containers capable of transmitting NIR light, collectively referred to hereinafter as "vessels") to determine if the vessels hold hazardous or contraband liquids. This is achieved by noninvasive NIR transmission or reflection imaging at one or more wavelength regions within the 850-1100 nm region, corresponding to NIR water absorption bands. Further, the system and method of the present invention can be utilized in the 850-1700 nm range, to identify chemicals and/or classes of compounds other than water-based liquids and organic liquids detectable in the 850-1100 nm region.

In particular, in a first embodiment of the present invention, a system for non-invasively inspecting vessels is provided comprising:

(a) a near-infrared (NIR) imaging means comprised of a detector array and one or more lenses disposed adjacent thereto;

(b) one or more NIR light sources disposed opposite the NIR imaging means; (c) one or more diffuser plates disposed adjacent the one or more NIR light sources; and (d) an optical wavelength selecting means capable of manually or electrically selecting a wavelength to be transmitted therethrough, said optical wavelength selecting means being disposed between the one or more lenses and the vessels, between the detector array and the one or more lenses, or between the one or more light sources and the vessels, wherein the vessels are illuminated by the NIR light sources, and an NIR image of the vessels is taken by the NIR imaging means.

In a second embodiment of the present invention, the system for non-invasively inspecting vessels of the first embodiment above is provided, further comprising:

(e) a computer processing means in communication with the NIR imaging means; and (f) a computer readable database in communication with the computer processing means. The computer readable database may contain just enough IR spectroscopic data for the computer processing means to determine simply whether the liquid is a water based liquid or organic based liquid. Alternatively, the computer readable database may comprise, but is not limited to, IR spectroscopic data for a plurality of known explosives, so as to enable spectral comparison of this spectral data base with measured peak absorbance values of the liquid in the vessel(s) being inspected.

In such an embodiment wherein the computer readable database comprises absorbance IR spectroscopic data for known explosive compositions, IR spectroscopic data in the range of 700 nm to 1600 nm for explosive compositions in their natural state (100% explosive composition), and in a mixed state (for example, the explosive composition in a solvent) is provided on the database. To measure peak absorbance values generally requires at least 3 measurement wavelength bands, and preferably at least 10 wavelength bands. In the embodiment of the invention where only one or two wavelengths are used in the inspection process, the system is capable of classifying the liquid as water or organic based, but explosives can not be identified.

In a third embodiment of the present invention, the system for non-invasively inspecting vessels of the second embodiment above is provided, further comprising:

(g) a computer readable medium including computer instructions for correlating measured peak absorbances to the IR spectroscopic data of the known explosive compositions, the computer instructions including instructions for:

determining the wavelength(s) of IR light to be used in the inspection of the vessels;

instituting the inspection of the vessel, comprising controlling operation of the NIR light sources and the NIR imaging means, so as to collect spectroscopic image test data. In particular, a spectral comparison identification measurement is performed noninvasively through the vessel to obtain NIR image data, and spectral measurements are then obtained from NIR image data;

transmitting of the spectroscopic image test data to the computer processing means;

querying the computer readable database, so as to compare the collected spectroscopic test data at image locations of high transmission through the vessel to the IR spectroscopic data of known explosive compositions;

determining which known explosive composition(s) correspond to the collected spectroscopic test data; and producing a user report comprising data concerning the known explosive composition(s) corresponding to the collected spectroscopic test data.

In a fourth embodiment of the present invention, the system for non-invasively inspecting vessels of the second embodiment above is provided, wherein the one or more NIR light sources emitting at different NIR wavelength bands are in communication with the computer processing means.

In a fifth embodiment of the present invention, the system for non-invasively inspecting vessels of the first embodiment above is provided, wherein the NIR imaging means is comprised of an Si-charged-coupled (Si-CCD) array detector digital camera or video camera, an Si-complementary metal-oxide-semiconductor (Si-CMOS) array detector digital camera or video camera, or an InGaAs photodiode array camera.

In a sixth embodiment of the present invention, the system for non-invasively inspecting vessels of the first embodiment above is provided, wherein the NIR imaging means is comprised of an NIR spectral imaging system.

In a seventh embodiment of the present invention, the system for non-invasively inspecting vessels of the first embodiment above is provided, wherein the NIR imaging means is comprised of a near-infrared Fourier-transform spectrometer having a two-dimensional array detector.

In an eighth embodiment of the present invention, the system for non-invasively inspecting vessels of the first embodiment above is provided, wherein the optical wavelength selecting means comprises one or more narrow bandpass optical interference filters having a center wavelength corresponding to a peak absorbance of water in the NIR range. Further, in a preferred embodiment, the system for non-invasively inspecting vessels of the eighth embodiment may further comprise one or more narrow bandpass optical interference filters having a center wavelength corresponding to specific selective frequencies corresponding to primary NIR absorption peaks of known explosives.

In a ninth embodiment of the present invention, the system for non-invasively inspecting vessels of the third embodiment above is provided, wherein the optical wavelength selecting means is a computer controlled electronically tunable filter.

In a tenth embodiment of the present invention, the system for non-invasively inspecting vessels of the eighth embodiment above is provided, wherein the optical wavelength selecting means comprises a plurality of movable narrow bandpass optical filters, such that the position of the filters, relative to input aperture of the NIR imaging means, may be controlled via the computer activated means.

In an eleventh embodiment of the present invention, the system for non-invasively inspecting vessels of the first embodiment above is provided, wherein said NIR light sources comprise one or more of a tungsten halogen lamps combined with narrow bandpass filters.

In a twelfth embodiment of the present invention, the system for non-invasively inspecting vessels of the first embodiment above is provided, wherein said NIR light sources comprise one or more NIR light emitting diodes (LED's).

In a thirteenth embodiment of the present invention, a method for non-invasively inspecting one or more vessels containing liquid is provided, comprising the steps of:

(a) blocking light from entering an NIR imaging means, and collecting a dark image via the NIR imaging means, so as to produce dark image data;

(b) illuminating a diffuser plate with one or more NIR light sources having a wavelength in the range of about 970-990 nm (corresponding to water) disposed adjacent a rear portion of the diffuser plate, without a vessel disposed between the NIR imaging means and the diffuser plate, and collecting an image of the diffuser plate, so as to produce background image data;

(c) placing one or more vessels between the NIR imaging means and the diffuser plate, illuminating the one or more vessels with the NIR light sources with light having a wavelength in the range of about 970-990 nm, and collecting a sample transmission image of the vessel via the NIR imaging means of the container, so as to produce sample transmission image data;

(d) calculating a pixel value for each of the dark image data, the background image data, and the sample transmission image data;

(e) calculating dark image corrected sample absorbance image pixel values, wherein the dark image corrected sample absorbance pixel value=−log(sample transmission image pixel value-dark image pixel value)/(background image pixel values-dark image pixel values);

(f) isolating a contiguous group of pixels in the dark corrected sample absorbance image corresponding to liquid area within the vessel, and calculating an average absorbance of the liquid area in the first sample transmission image;

(g) calculating the diameter of the vessel;

(h) calculating a diameter normalized absorbance (DA) of the vessel using the following formula:

$$DA=(\text{optical absorbance measured in step}(c))/(\text{vessel diameter measured in step }(g));$$

(i) conducting a threshold normalized absorbance analysis by comparing the DA calculated in step (h) to a threshold normalized absorbance value for water-based liquids, and determining whether the DA meets or exceeds the threshold value range for water-based liquids, where a DA that meets or exceeds the water based liquid threshold normalized absorbance value indicates the presence of an aqueous based liquid; and (j) producing a user report comprising threshold normalized absorbance analysis data.

In a fourteenth embodiment of the present invention, the method for non-invasively inspecting a vessel containing liquid of the thirteenth embodiment above is provided, comprising the further step of:

(k) comparing each DA calculated in step (h) to one or more standard DA ranges for organic liquids, to determine whether the vessel contains a known organic liquid.

In a fifteenth embodiment of the present invention, the method for non-invasively inspecting a vessel containing liquid of the thirteenth embodiment above is provided, wherein the standard DA range for a water-based liquid is about 0.177-0.194 absorbance units/cm.

In a sixteenth embodiment of the present invention, the method for non-invasively inspecting a vessel containing liquid of the fourteenth embodiment above is provided, wherein the standard DA range for organic liquids is about 0.021-0.043 absorbance units/cm.

In a seventeenth embodiment of the present invention, a method for non-invasively inspecting a vessel containing liquid is provided, comprising the steps of:

(a) blocking light from entering an NIR imaging means, and collecting a dark image via the NIR imaging means, so as to produce dark image data;

(b) illuminating a diffuser plate with one or more NIR light sources having a wavelength in the range of about 970-990 nm disposed adjacent a rear portion (rear side) of the diffuser plate, without a vessel disposed between the NIR imaging means and the diffuser plate, and collecting an image of the diffuser plate, so as to produce first background image data;

(c) placing one or more vessels between the NIR imaging means and the diffuser plate, illuminating the one or more vessels with the NIR light sources with light having a wavelength in the range of about 970-990 nm, and collecting a first sample transmission image of the one or more vessels via the NIR imaging means of the container, so as to produce sample transmission image data;

(d) illuminating a diffuser plate with one or more NIR light sources having a wavelength in the range of about 850-1700 nm, disposed adjacent a rear portion * rear side?* of the diffuser plate, without a vessel disposed between the NIR imaging means and the diffuser plate, and collecting an image of the diffuser plate, so as to produce second background image data;

(e) illuminating the one or more vessels with the NIR light sources with light having the wavelength utilized in step (d) above, and collecting a second sample transmission image of the vessel via the NIR imaging means of the container, so as to produce second sample transmission image data;

(f) calculating a pixel value for each of the dark image data, the first background image data, the first sample transmission image data, the second background image data, and the second sample transmission image data;

(g) calculating a dark image corrected sample absorbance pixel value, wherein the dark image corrected sample absorbance pixel value=−log [(sample transmission image pixel value−dark image pixel value)/(background image pixel values−dark image pixel values)];

(h) isolating a contiguous group of pixels in the dark image corrected sample absorbance corresponding to liquid area within the vessel, and calculating a first average absorbance of the liquid area;

(i) isolating a contiguous group of pixels in the second sample transmission image corresponding to liquid area within the vessel, and calculating a second average absorbance of the liquid area;

(j) calculating the diameter of the vessel;

(k) calculating a differential diameter normalized absorbance (differential DA) of the vessel using the following formula:

Differential *DA*=(optical absorbance measured in the first sample transmission image in step(*c*)−optical absorbance measured in the second sample transmission image in step (*e*))/(vessel diameter measures in step (*j*));

(l) conducting a threshold normalized absorbance analysis by comparing the differential DA calculated in step (k) to a threshold normalized absorbance value for water-based liquids, and determining whether the DA meets or exceeds the threshold value range for water-based liquids; and (m) producing a user report comprising threshold normalized absorbance analysis data.

In an eighteenth embodiment of the present invention, the method for non-invasively inspecting a vessel containing liquid of the seventeenth embodiment above is provided, comprising the further step of:

(n) comparing the Differential DA calculated in step (j) to one or more standard DA ranges for organic liquids, to determine whether the vessel contains a known organic liquid.

In a nineteenth embodiment of the present invention, the method for non-invasively inspecting a vessel containing liquid of the seventeenth embodiment above is provided, wherein the one or more NIR light sources and diffuser plate are disposed adjacent the imaging means, so as to reflect light off of the vessel, said NIR imaging means producing an image in steps (c) and (e) based on the reflected light; and wherein −log(reflectance) is calculated instead of absorbance, and reflectance is given by: reflectance=(sample reflected image−dark image)/(background image−dark image).

In a twentieth embodiment of the present invention, the method for non-invasively inspecting a vessel containing a liquid of the seventeenth embodiment above is provided, wherein the vessel is illuminated in steps (d) and (e) with NIR light having a wavelength in the range of about 850-930 nm. The wavelength ranges 850-930, or 1040-1100, both are chosen to be away from the peak of the water absorption and centered at 970-990 nm, and either of these ranges provide a baseline absorbance to subtract from the absorbance at 970-990 nm, in order to produce a differential absorbance that measures the height of the water absorption band.

In a twenty first embodiment of the present invention, the method for non-invasively inspecting a vessel containing a liquid of the seventeenth embodiment above is provided, wherein the vessel is illuminated in steps (d) and (e) with NIR light having a wavelength in the range of about 1040-1100 nm.

In a twenty second embodiment of the present invention, the method for non-invasively inspecting a vessel containing a liquid of the seventeenth embodiment above is provided, wherein the vessel is illuminated in steps (b)-(e) with NIR light in two separate wavelength bands, each band having a wavelength in the range of about 85-1700 nm.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 19 is a side view of an embodiment of the system of the present invention, illustrating the simultaneous inspection of a group of vessels, where the illumination source is located below the group of vessels, and the camera is located above the group of vessels. The path of the light going through the vessels enters each vessel from the bottom and exits through the top thereof, such that the light path avoids going through multiple labels on the vessels (labels are normally present on the sides of bottles, and not on the top or bottom of a bottle or other container).

DETAILED DESCRIPTION OF THE INVENTION

The present invention provides a system for non-invasively inspecting one or more vessels capable of transmitting near-infrared (NIR) light, utilizing transmission or reflection imaging of the vessels at visible and NIR wavelengths, so as to identify liquids/compositions contained within the vessels. The system and method are effective in inspecting any vessel capable of transmitting NIR light, such as glass and plastic bottles, paper containers, and cardboard containers. Further, the system is not limited to the inspection of certain vessel shapes, i.e., any shape vessel capable of transmitting IR light may be inspected with the system and method of the present invention.

Figure 1:
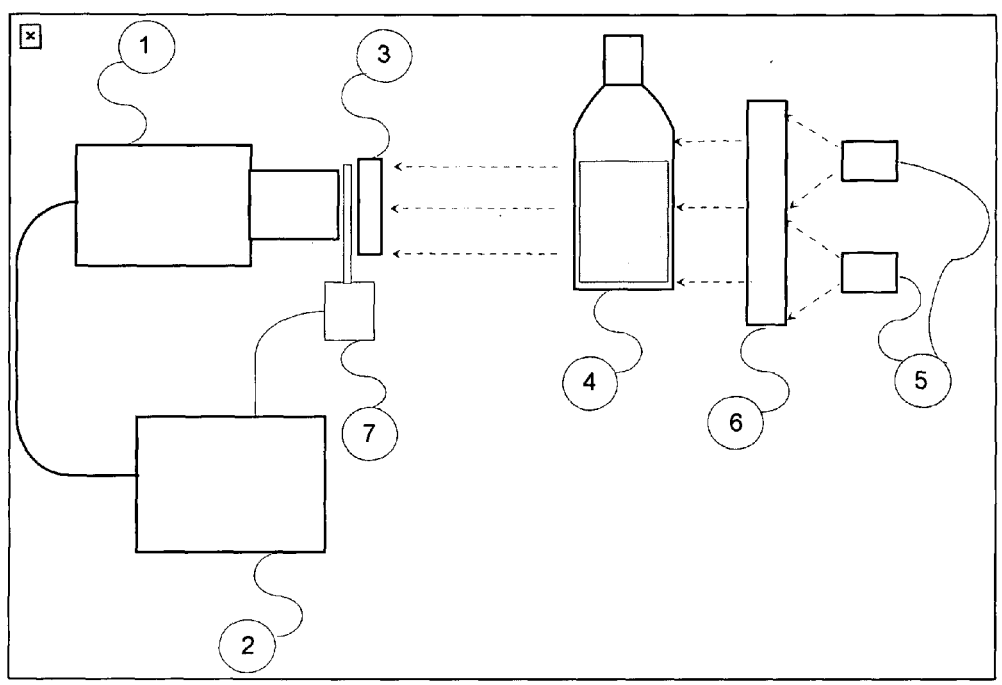
FIG. 1 is a box diagram illustrating the system for non-invasively inspecting vessels of the present invention
Figure 2:
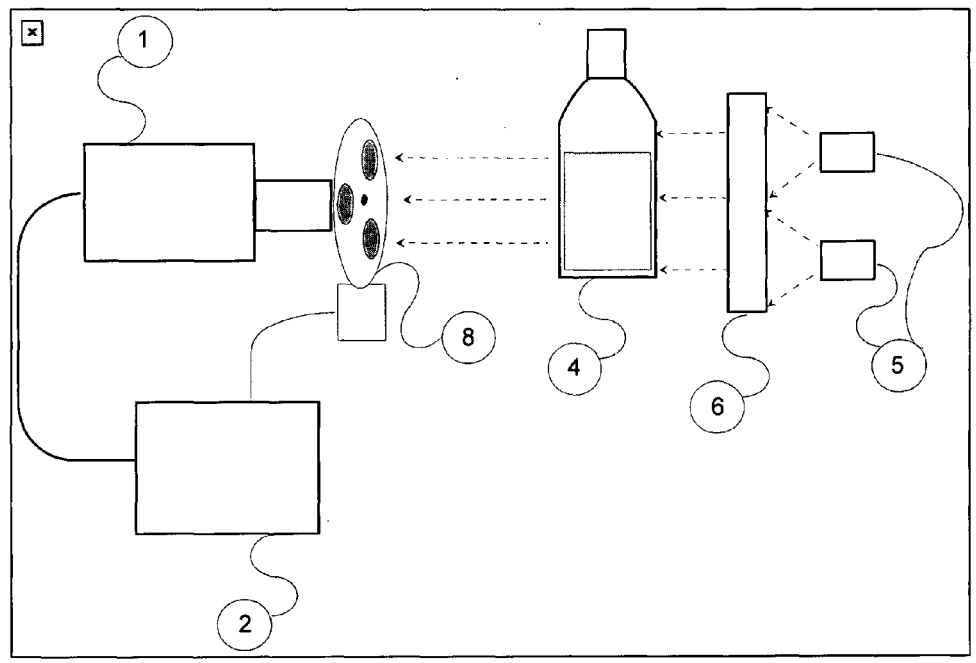
FIG. 2 is a box diagram of the system for non-invasively inspecting vessels of the present invention, illustrating an embodiment of the present invention utilizing differential wavelength NIR transmission imaging inspection of liquids in vessels, having, as the optical wavelength selecting means, a computer or microprocessor controlled motorized wheel with multiple narrow bandpass optical filters (8), in place of the single narrow bandpass optical interference filter (3) shown in FIG. 2. In particular, the computer controlled filter wheel 8 in FIG. 3 contains two narrow bandpass NIR filters, as well as a metal disk to act as a shutter in one of the three filter positions, in place of the single narrow bandpass filter 3 and the computer controlled shutter 7 shown in FIG. 2.
Figure 3:
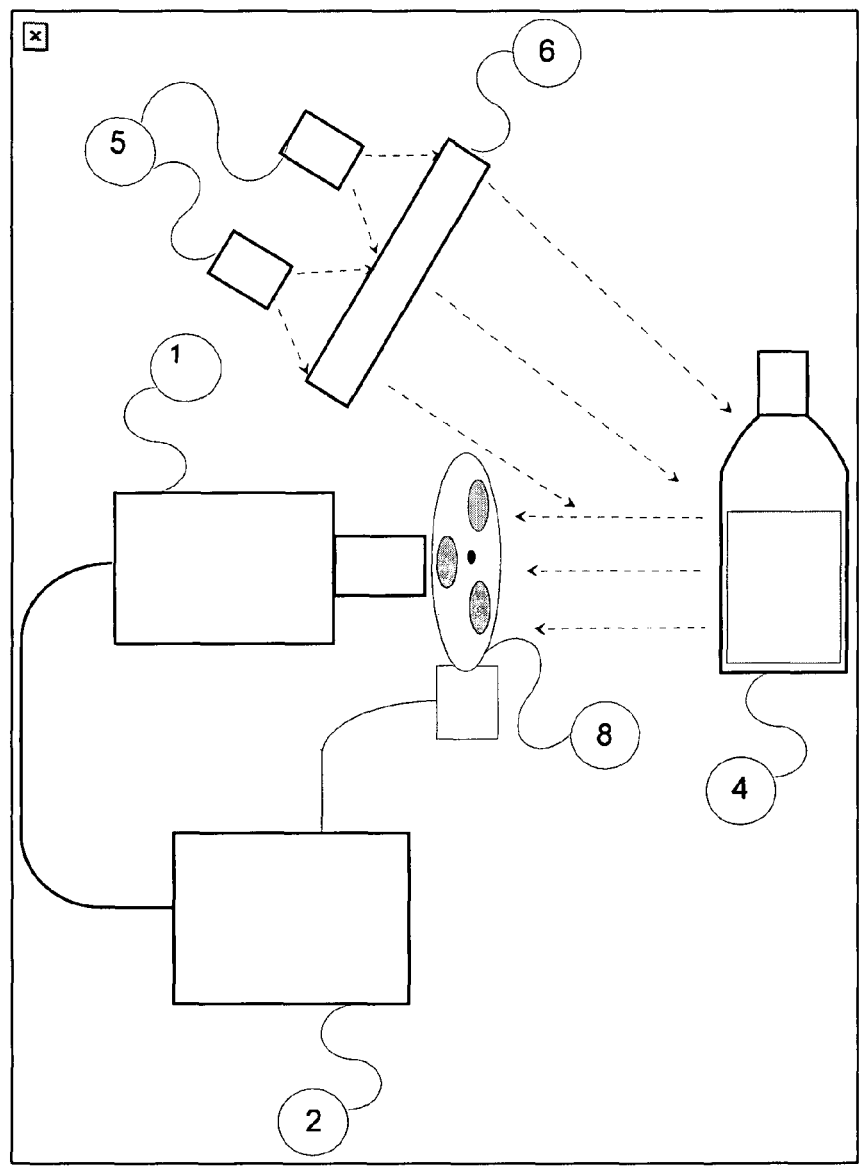
FIG. 3 is a box diagram of the system for non-invasively inspecting vessels of the present invention, illustrating a preferred system for differential wavelength NIR reflection imaging inspection of liquids in vessels.

The system of the present invention can be configured to inspect the vessel by reflection or transmission of NIR light at/through the vessel. In particular, the system of the present invention may have a linear configuration, as shown in FIG. 1 and FIG. 2, or a folded configuration, as shown in FIG. 3. Further, advantageously, the system of the present invention is capable of "standoff" inspection of vessels, i.e., the system requires no contact with the vessels to be inspected, but rather may be positioned in a standoff position from the vessels.

In practice, the system of the present invention functions to first test whether the liquid in the vessel is benign (such as water or a water-based composition). This first step is defined as the primary detection step. In a preferred embodiment, if the composition is determined not to be benign, the system then conducts a secondary inspection step. Although not required in the basic embodiment of the present invention, the secondary inspection step, involving conducting a secondary analysis, enables the determination of the liquid chemical identity.

Specifically, this secondary inspection step involves directing multiple wavelengths of IR light at/through the vessel, and collecting several images of the vessel at different wavelengths. Such secondary inspection step includes differential imaging techniques, which enable the system and method to determine, by correlating the measured absorbance data with data of known explosives stored on a computer database, whether an explosive composition is contained within the vessel, and if so, which explosive composition it is.

In particular, as illustrated in FIG. 1, a system for non-invasively inspecting one or more vessels 10 is provided, comprised of a near-infrared (NIR) imaging means 1, one or more NIR light sources 5, and a diffuser plate 6.

The NIR imaging means 1, although not specifically illustrated, is generally comprised of a detector array and one or more lenses disposed adjacent thereto. In practice, the NIR imaging means may be comprised of, but is not limited to, a Si-charged-coupled (Si-CCD) array detector digital camera or video camera, an Si-complementary metal-oxide-semiconductor (Si-CMOS) array detector digital camera or video camera, or an InGaAs photodiode array camera. Alternatively, the NIR imaging means is comprised of an NIR spectral imaging system, such as a near-infrared Fourier-transform spectrometer having a two-dimensional array detector or a NIR camera combined with an electronically tunable narrow bandpass filter. Preferably, the NIR imaging means is silicon-CCD (charged coupled detector) array camera, which can be used for screening most types of clear liquids in containers by transmission imaging or for screening opaque liquids with a high particulate content by NIR reflection imaging. Such opaque liquids would include milk products, including baby formula, and orange juice.

Two NIR light sources 5 are illustrated in FIG. 1, but one or more can be utilized. The NIR light sources are preferredly one or more tungsten halogen lamps. ** it is much more cost effective to have the narrow bandpass filters in front of the camera lens instead of in front of the tungsten halogen lamps. Instead of using tungsten halogen lamps for the light sources 5, as shown in FIG. 1, NIR light-emitting diode (LED) sources with, for example, a single emission band close to 980 nm, can alternatively be used (for example LED's with a 970 nm center wavelength are commercially available). If LED sources are used, the narrow bandpass filter 3 shown in FIG. 1 could be eliminated, however this filter (3) still could be used to obtain increased selectivity in the inspection measurement.

The LED source can consist of a single LED or an array of LED's emitting at the same wavelength band.

In the preferred embodiment of the present invention involving two wavelength band transmission imaging, LED sources 5 emitting at two different NIR wavelength bands can be used in place of both the broadband light sources (such as tungsten halogen lamps) and the optical wavelength selecting means (i.e., the filter wheel) 8 shown in FIG. 2 containing three narrow bandpass NIR filters. Narrow bandpass filters can be used in front the two different center wavelength LED source to provide a narrower wavelength band emission range for each of these sources. The LED sources emitting at the two wavelength bands can also be used without any narrow bandpass filters or other optical filters.

In a further alternative embodiment of the present invention, the NIR light sources may be one or more NIR light emitting diodes (LED's), or a combination of NIR LED's and tungsten halogen lamps with narrow bandpass optical interference filters.

Although one diffuser plate 6 is shown in FIG. 1, one or more diffuser plates, disposed adjacent the one or more NIR light sources, can be utilized. The vessel 4 is illuminated by the NIR light sources 5, via the diffuser plate 6, and an NIR image of the container is taken by the NIR imaging means 1.

As described above, a basic construction of the system for non-invasively inspecting vessels of the present invention is comprised of an NIR imaging means, one or more NIR light sources, a diffuser plate, and an optical wavelength selecting means. In such a basic construction, the operator of the system must be trained to a level sufficient to approximate, with visual inspection, when a threshold for absorption at certain wavelengths is reached for NIR image of a liquid in a vessel. Then, the operator must correlate these thresholds to standard guidelines to identify the compositions be inspected.

Naturally, such an inspection method will have a lower reliability than a computer controlled system.

Thus, in a preferred embodiment, as illustrated in FIGS. 1-3, a computer processing means 2 is provided in communication with the NIR imaging means. The computer processing means 2 may further be in communication with the NIR light sources 5, the optical shutter 7, and/or the optical wavelength selecting means 8. The computer processing means may be any information processing device, including but not limited to a personal computers (PC), personal digital assistants (PDAs), hand held computer, palm top computer, lap top computer, or a microprocessor based digital circuit system. Preferably, the PC is an IBM or compatible PC workstations running a Microsoft Windows or LINUX operating system, one or more Macintosh computers running a Mac OS operating system, or an equivalent.

Further, preferredly, as shown in FIG. 1, one or more narrow bandpass optical interference filters 3 are disposed between the one or more lenses of the NIR imaging means 1 and the vessel 4. Preferredly, the one or more narrow bandpass optical interference filters are bandpass optical filters having a center wavelength corresponding to a peak absorbance of water in the NIR range, and one or more narrow bandpass optical interference filters having a center wavelength corresponding to specific selective frequencies corresponding to primary IR absorption peaks of known explosives.

Alternatively, the one or more narrow bandpass optical interference filters 3 can be disposed between the detector array of the NIR imaging means 1 and the one or more lenses of the imaging means 1, or between the one or more light sources 5 and the container 4. In any event, the narrow optical bandpass optical inference filter 3 must be positioned so as to filter the light in the wavelength region of interested before said light enters the detector array of the NIR imaging means 1.

Figure 4A:
FIG. 4(a) is a transmission image of two polyethyelene terephthalate (PETE) bottles, one containing cranberry juice and one containing kerosene, taken at visible wavelengths using a low-cost Sony® Si-CCD video camera (camcorder), which illustrates the similar color and transmission of cranberry juice an kerosene at visible wavelengths.
Figure 4B:
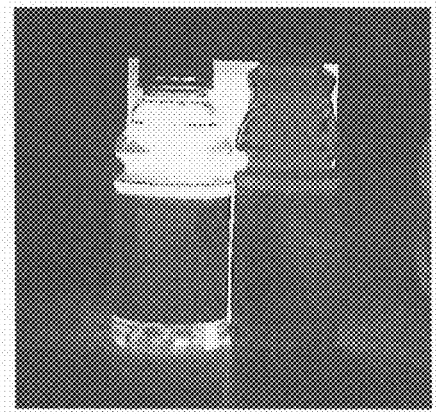
FIG. 4(b) is a transmission image of the PETE bottles containing cranberry juice and kerosene shown in FIG. 4(a), taken with the Sony® Si-CCD video camera used in FIG. 4(a), but in the NIR range, using the enhanced gain and enhanced NIR response nighttime imaging (nightshot) mode of the camera, and with a 980 nm narrow bandpass interference filter disposed in front of the camera lens. The NIR images show high transmission for the kerosene (bottle on left) vs. low transmission for the cranberry juice (bottle on right).

As illustrated in FIG. 2 and FIG. 3, if more than one narrow bandpass optical interference filter is being, then an optical wavelength selecting means 8 is provided, wherein the filters are mounted in some type of movable fixture that allows switching between the filters, such that the light may be filtered to the desired wavelength region before entrance of same into the input aperture of the NIR imaging means 1. Preferredly, the optical wavelength selecting means includes a computer or microprocessor controlled motorized wheel with multiple narrow bandpass optical filters 8, as illustrated in FIG. 3 and FIG. 4, is provided. This motorized wheel 8 is in communication with the computer processing means 2, so as to be controlled thereby.

Alternatively, the optical wavelength selecting means may include an electrically tunable narrow bandpass filter, wherein the wavelength of the light transmitted therethrough can be adjusted based on an electrical input to the filter. Although generally more costly than a mechanical means of wavelength filtering, such an electrically tunable filter may have a broader range of possible wavelengths.

Figure 5A:
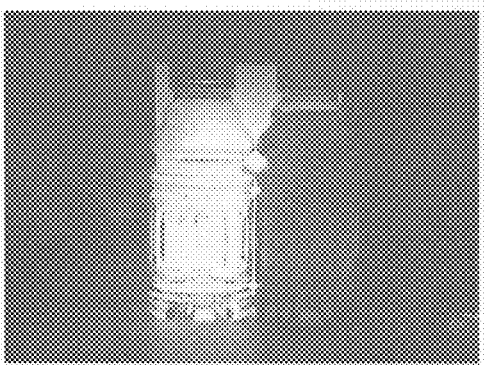
FIG. 5(a) is an NIR transmission image, measured with a Sony® Si-CCD camera, of gasoline (left) and white grape juice (right) in 16 oz PETE bottles, at 980 nm using the nighttime imaging mode of the camera.
Figure 5B:
FIG. 5(b) is a transmission image in the visible wavelength range, measured with the Sony® Si-CCD camera mentioned above, of the PETE bottles containing gasoline and white grape juice shown in FIG. 5(a).
Figure 6A:
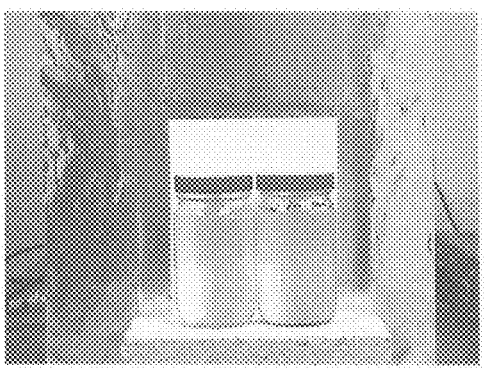
FIG. 6(a) is a transmission image taken in the visible wavelength range of water (left bottle) and nitromethane (right bottle) in 200 ml clear glass bottles, measured with the Sony® Si-CCD camera mentioned above.
Figure 6B:
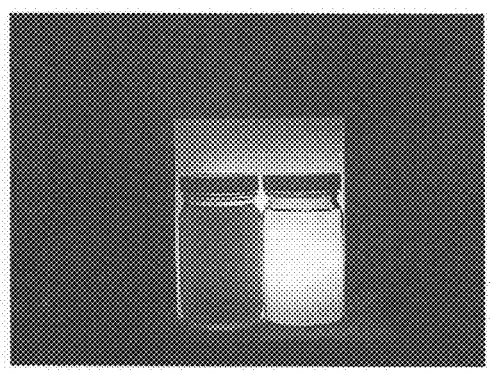
FIG. 6(b) is an NIR transmission image of the water (left bottle) and nitromethane (right bottle) shown in FIG. 6(a), measured with the Sony® Si-CCD camera mentioned above, having a 980 nm narrow bandpass filter disposed in front of the lens thereof, using the nighttime imaging mode of the camera.

In addition, or alternative to, the optical wavelength selecting means, as illustrated in FIG. 1, an optical shutter 7 may be disposed adjacent the NIR imaging means 1, and in communication with the computer processing means 2. Preferredly, the optical shutter 7 is a computer controlled, electrically activated optical shutter, said optical shutter being in communication with the computer processing means. The optical shutter 7 operates to either block light from entering the input aperature of the NIR imaging means 1, so as to collect a dark image, or allow entrance of light into the input aperture. The dark image data is subtracted from the images of the bottles being inspected, so as to produce better quality images. However, as illustrated in FIGS. 4-6, images which are sufficient to inspect vessels can be obtained without the dark image subtraction. The optical shutter 7 merely enables the operator to collect and subtract a dark image, thereby producing a better image and more accurate results.

In FIG. 1, the system of the present invention is operating in a transmission imaging mode, i.e., light is transmitted through the vessel 4 being inspected before reaching the NIR imaging means 1. In FIG. 2, a system for inspection of vessels to differentiate their contents between aqueous and organic liquids based on NIR differential wavelength transmission imaging is illustrated. Further, if such system includes three or more narrow bandpass filters transmitting at different wavelength bands, permitting measurement of spectral imaging data at 3 or more wavelength bands, and is in communication with a computer database, and has the computer readable medium including computer instructions for correlating measured peak absorbances to the IR spectroscopic data of the known explosive compositions operating on the computer processing means, the contents in the vessel may be compared to known explosive compositions, to determine whether a known explosive is present.

Figure 24:
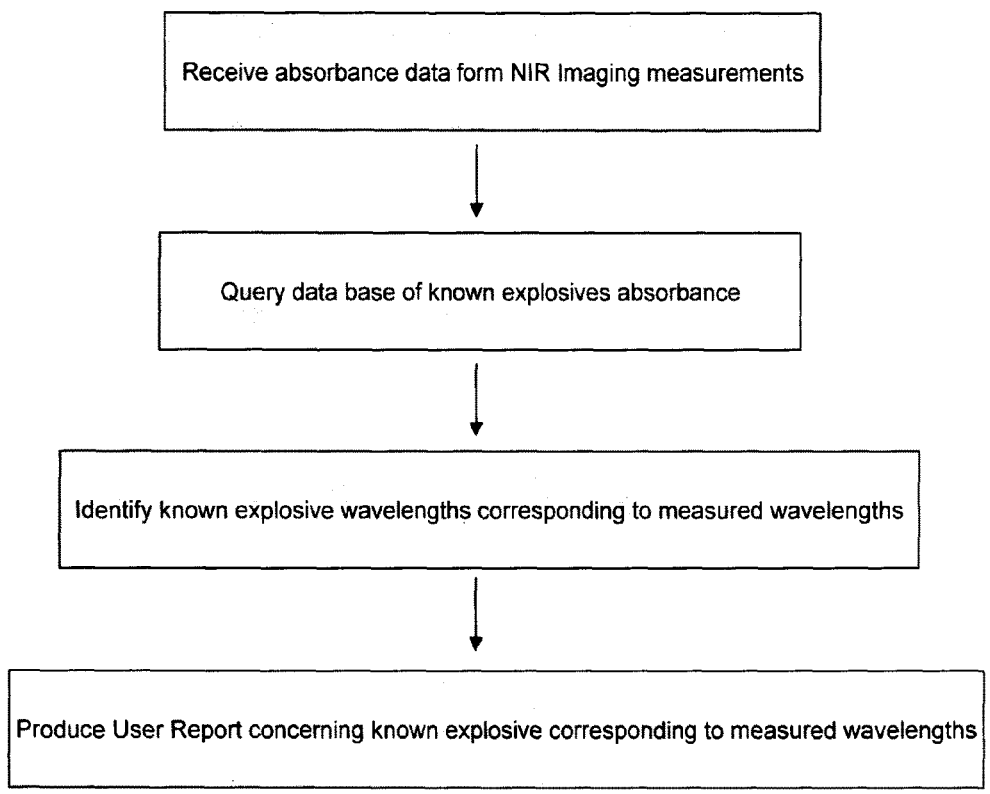
FIG. 24 is a functional flow diagram illustrating the general functional steps taken by the computer instructions of the present invention.

In particular, the present invention provides a computer readable medium including computer instructions (i.e., a computer program application) for correlating (comparing) measured peak absorbances to the IR spectroscopic data of known explosive compositions, identifying which known explosive compositions have peak absorbances identical or similar to the measured peak absorbances, and producing a user report concerning same. The basic functional steps taken by such computer instructions are illustrated in FIG. 24. Such computer readable medium including computer instructions must be capable of being run on the computer processing means of the system of the present invention, or a separate computer processing means in communication therewith.

Figure 23:
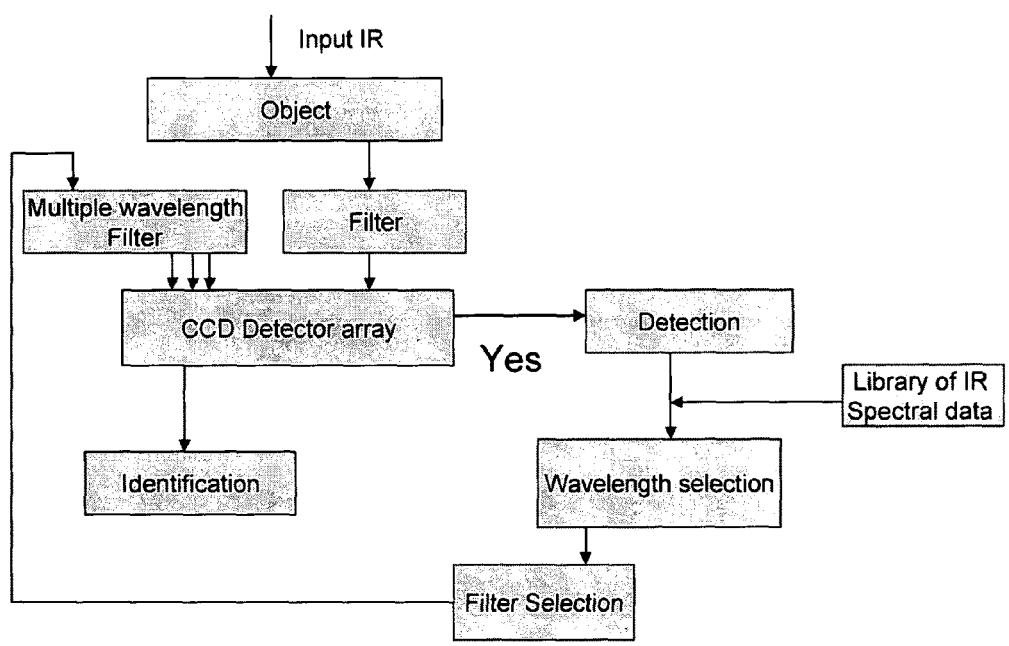
FIG. 23 is a flow diagram illustrating the functional steps taken by the system for non-invasively inspecting one or more vessels capable of transmitting IR light of the present invention during the inspection process.

As illustrated in FIG. 24, such computer readable medium including computer instructions is comprised of computer instructions including instructions for:

(1) Determining the wavelength(s) of IR light to be used in the inspection of the vessels. In particular, as illustrated in FIG. 23, the computer processing means first determines which wavelengths to use to conduct the inspection of the vessel, based on peak absorbances for water, organic-based liquids, and known explosive. Although identification of specific explosive compositions is desirable, it is frequently satisfactory to conduct a primary inspection so as to simply determine whether the liquid in the inspected vessel is water or organic based. However, in a preferred embodiment, identification of explosives may be conducted, involves inspection using 3 or more, and preferably at least 10 or more, wavelengths bands. In relation to the primary inspection mentioned above, spectral measurement at 10 or more wavelength bands (vs. 2 wavelength bands) involves substantially increased measurement time and increased system cost.

2. Instituting the inspection of the vessel. Such instructions allow the computer processing means to control the operation of the NIR light sources, narrow bandpass filters, and the NIR imaging means, i.e., to turn on and off same. This allows the system to control the timing and collecting characteristics of the spectroscopic test data.

3. Transmitting of the spectroscopic test data to the computer processing means. This enables the computer processing means to receive the spectroscopic test data from the NIR imaging and optical bandpass filter means, and store same in a readable format.

4. Querying the computer readable database, so as to compare the collected spectroscopic test data to IR spectroscopic data of water and organic based liquids and known explosive compositions. Specifically, these instructions allow the computer processing means to compare the spectroscopic test data collected during the inspection of the vessel to a database of spectroscopic data of known compositions, including water, organic liquids, and explosive compositions.

5. Determining which known compositions, including explosive compositions, correspond to the collected spectroscopic test data.

6. Producing a user report comprising data concerning the water or organic based liquid identity and any known explosive composition(s) corresponding to the collected spectroscopic test data. In particular, these instructions enable the compilation of a user report containing a list of peak absorbances identified within the collected spectroscopic test data, and a list of known compositions corresponding to those peak absorbances. In embodiments where only 1 or 2 wavelength bands are measured, spectral peak position data is not produced and the report would only include information on the water or organic based nature of the liquid being inspected.

In contrast to the transmission type configurations described above, as illustrated in FIG. 1 and FIG. 2, the present invention provides a two wavelength imaging system that operates in the reflection imaging mode. In particular, in such an embodiment, as illustrated in FIG. 3, the light sources 5 and the diffuser plate 6 are positioned on the same side of the vessel 4 being inspected as the NIR imaging means 1, to permit imaging via reflection of NIR light off of the vessel. This embodiment enables inspection of vessels to differentiate their contents between aqueous and organic liquids based on NIR differential wavelength reflection imaging. This system can be used for screening vessels containing, for example, milk products, baby formula, and orange juice.

According to the present invention, the steps to be followed for determining whether a liquid in a vessel under inspection is water based or organic using the system of the present invention, as shown in FIG. 2, are as follows:

Step (1): Block light from entering the NIR imaging means 1, by closing the optical shutter 7, collect a dark image (using a single image collection of about 0.02-1.0 second collection time) so as to produce dark image data, and transfer the dark image data to the computer processing means 2;

Step (2): illuminate the diffuser plate 6 with one or more NIR light sources 5 having a wavelength in the range of about 970-990 nm disposed adjacent a rear portion of the diffuser plate 6 (using a single image collection time in the range of about 1.0-0.02 seconds), without a vessel disposed between the NIR imaging means and the diffuser plate, collect an image of the diffuser plate, so as to produce background image data, and transfer the background image data to the computer processing means 2. The background image data is used to correct for nonuniformities in the illumination distribution and the camera detector array response. Steps (1) and (2), generally, only have to be conducted about once every 60 minutes;

Step (3): Place one or more vessels 4 between the NIR imaging means 1 and the diffuser plate 6, illuminate the one or more vessels 4 with the NIR light sources 5 with light having a wavelength in the range of about 970-990 nm, collect a sample transmission image of the vessel 4 via the NIR imaging means 1 using a single image collection time of about 1.0-0.02 seconds, so as to produce sample transmission image data, and transfer the sample transmission image data to the computer processing means 2;

Step (4): Calculate a pixel value for each of the dark image data, the background image data, and the sample transmission image data. The pixel values are automatically collected and calculated from the imaging means 1 by the computer processing means 1 through a digital interface (such as a USB, or Ethernet, or IEEE-1394 interfaces), or through a analog interface followed by a analog to digital conversion circuit or frame grabber circuit which outputs into the computing means Step (5): Calculate a dark image corrected sample absorbance image, wherein the dark image corrected sample absorbance=−log(sample transmission image pixel value-dark image pixel value)/(background image pixel values-dark image pixel values);

Step (6): Isolate a contiguous group of pixels in the dark corrected sample absorbance image corresponding to liquid area within the vessel (preferably an area without interference from labels disposed on the vessels), and calculate an average absorbance of the liquid area in the first sample transmission image. The isolation of the contiguous group of pixels may either be conducted via manual selection by an operator (using a computer mouse or similar pointing device), or preferably by automated selection via an artificial intelligence routine;

Step (7): Calculate the diameter of the vessel. In particular, first, the distance from the vessel 4 to the NIR imaging means 1 is determined using a conventional range-finder device (such as a laser range-finder or an ultrasonic rangefinder). Then, the vessel image diameter in pixels is measured from the image collected on the computing means.

The image diameter in pixels from the image collected on the computing means is determined from the horizontal distance (in pixels) in the image over which 5 or more consecutive horizontal image line profiles have a significant absorbance dip (which would correspond to optical absorption by the vessel material and the vessel contents) that is greater than the root-mean-square image noise in the background image by a factor of 2 or more. Then the image diameter in pixels is converted into the real vessel diameter using the equation:

$$\text{Diam}_{real} = \text{Diam}_{image} \times W \times \text{Demag}$$

where $\text{Diam}_{real}$ is the actual vessel diameter in some standard units such as cm, $\text{Diam}_{image}$ is the image diameter of the vessel in image pixels, W is the detector array pixel width (W) in cm/pixel, Demag is the demagnification factor of the vessel image which is calculated from the distance (Dist) in cm between the vessel and the imaging means lens, and from the lens focal length (FL) in cm, where Demag=FL/Dist. calculating the diameter of the vessel;

Step (8): calculating a diameter normalized absorbance (DA) of the vessel using the following formula:

$$DA = (\text{optical absorbance measured in step}(c))/(\text{vessel diameter measure in step (7)});$$

This DA is calculated only for the contiguous group of pixels in the liquid area at determine in step (6).

Step (9): Conduct a threshold normalized absorbance analysis by comparing the DA calculated in step (8) to a threshold diameter normalized absorbance value for water-based liquids, and determine whether the DA meets or exceeds the threshold value range for water-based liquids, where a DA that meets or exceeds the water based liquid threshold DA value indicates the presence of an aqueous based liquid. Determine whether the liquid area DA is above the threshold value for water based liquids; and If the liquid area normalized absorbance is above the threshold value, then the liquid is declared to be water-based (this data is preferably displayed to a user on the computer display). If the liquid area normalized absorbance is less than an organic liquid threshold value, then the liquid is declared organic. The threshold diameter normalized absorbance value will be in the range of 0.14-0.04 ABS units/cm).

Alternatively, the threshold normalized absorbance analysis of the selected liquid area image pixel data can be conducted using two absorbance thresholds, i.e., T1 for water based liquids and T2 for organic based liquids. If the normalized absorbance is above T1, then the liquid is declared water based, and if the normalized absorbance is less than T2, then the liquid is declared organic based. If the normalized absorbance is between T1 and T2, then the liquid identity is declared to be uncertain. The T1 value will be approximately 0.13 ABS units/cm (with a possible T1 range of 0.10-0.16) and the T2 value will be approximately 0.06 ABS units/cm (with a possible T2 range of 0.04-0.09).

In another preferred embodiment of the present invention, the optical inspection uses a differential transmission imaging measurement between two near-infrared imaging wavelengths. This embodiment utilizes two imaging wavelength bands in a differential imaging measurement, which results in a reduction of interference from labels disposed on vessels, or vessel walls containing light scattering or absorbing pigments. Vessel labels or vessel walls can contain light scattering or absorbing pigments, which can produce substantial NIR absorption losses from the light scattering or absorption effects.

In particular, the differential wavelength method helps remove image contributions from interfering backgrounds, such as vessel labels, or light scattering and absorption from pigments in the vessel walls. These interfering backgrounds from the vessel normally produce very similar absorption/light scattering loss in the NIR images at the two closely spaced wavelengths used for the differential wavelength imaging method, while water contained in a vessel has a large absorbance difference between these two wavelengths.

This variation of the present invention employs one NIR wavelength at the peak of a water absorption band (preferably the 980 nm band), and one NIR wavelength just above or below the absorption band (preferably about either 1050 or 920 nm for the 980 nm water absorption band). The NIR transmission images at the two selected wavelengths are converted to absorbance units after first collecting a dark image with the light blocked from entering the camera with a shutter or similar device, and a background image at both of the wavelengths with the illumination source on but no vessel present.

The conversion of the dark, background and sample transmission images into a corrected image in absorbance units is described above. The final differential image, which will be referred to as a "differential wavelength image", consists of the difference of the absorbance images at the two wavelengths corresponding to wavelengths on and just off the NIR water absorption band (image at 980 nm minus the image at 1050 or 920 nm).

As discussed above, FIGS. 2 and 3 illustrates embodiments of the system of the present invention that can be used for differential wavelength imaging. The two NIR image narrow wavelength bands can be selected through the use of the optical wavelength selecting means (such as a computer or microprocessor controlled filter wheel) 8 disposed in front of the NIR imaging means 1, in place of the single fixed filter 3 shown in FIG. 1. Images are collected in sequence at the two wavelengths via the computer processing means 2 selecting the appropriate filter wheel position for the required image collection time.

If a filter wheel is used, one wheel position can contain a metal disk to block the light to the camera (i.e., to act as an optical shutter) for a dark image measurement, thereby eliminating the need for the optical shutter 7 shown in FIG. 1. In yet another preferred embodiment of the present invention, differential wavelength imaging in the reflectance mode is employed for liquids that contain high concentrations of particulates. This embodiment can be used for inspecting liquids in vessels that contain substantial concentrations of suspended particulates (including colloidal liquids), which prevent significant transmission of light through the liquids when contained in vessels. This preferred embodiment involves differential wavelength imaging in the NIR wavelength range using reflection imaging as opposed to transmission imaging described above.

The NIR light illuminates the exterior of vessels containing liquids with particulates, and then the NIR light is backscattered by the particulates after penetrating a finite distance through the liquid. The backscattered NIR light can then be imaged at two wavelengths to distinguish aqueous vs. organic based liquids that contain particulates. The reflection imaging arrangement for this preferred embodiment is similar to that given in FIG. 2, except that the light source and the camera are both on the same side of the bottle or container being inspected.

The single wavelength embodiment of the present invention (where single wavelength transmission imaging is used) can be conducted without subtracting a dark current measurement and normalizing with a background image of the light source. The raw transmitted intensity image can be used instead of the absorbance image. The NIR images shown in FIGS. 4(a)-6 were collected in this manner without correction using dark current and illumination background images.

Transmission images can be measured at the two NIR wavelength bands defined by the two different wavelength LED sources (or the sources plus associated narrow bandpass filters) by turning on the LED sources in sequence, in which one image is measured at the first LED wavelength band with the first LED source on, and the second LED source off, and then a second image is measured at the second wavelength band where only the second LED source is turned on. Then the differential wavelength transmission image can be generated by first processing the two images into absorbance units, and then subtracting them as described above. The two LED sources can consist of a single LED of each of the two types, or an array of LED's emitting at each of the two wavelength bands.

In the embodiment of the present invention involving the two NIR wavelength band reflectance imaging, as illustrated in FIG. 3, LED sources at two different NIR wavelength bands can be used in place of both the broadband light sources (such as tungsten halogen lamps) and the optical wavelength selecting means (i.e., the filter wheel containing the two narrow bandpass NIR filters). As described above, narrow bandpass filters may be required in front the two LED source to provide a narrower wavelength band range. The final differential wavelength reflection image can be measured following the same procedure described above, except that the images are measured in the reflectance mode as illustrated in FIG. 3. The two LED sources can consist of a single LED of each of the two types, or an array of LED's emitting at each of the two wavelength bands.

The preferred embodiment of the present invention involving the differential wavelength transmission and reflectance imaging can be conducted without measuring and subtracting a dark image. The differential wavelength transmission and reflectance imaging variations of the system of the present invention, as illustrated in FIG. 2 and FIG. 3, respectively, can both be combined into a single vessel inspection system and method that inspects vessels by both transmission and reflectance imaging. This can be performed with a single NIR camera, where the transmission and reflectance imaging measurements are conducted in sequence rather than simultaneously.

For vessels that contain either clear liquids or liquids with substantial amounts of suspended particulates, the combined NIR transmission and reflectance imaging system can first check, in the transmission mode, the magnitude of the diameter corrected single wavelength band absorbance at either 920 nm or 1050 nm of liquid containing areas of a vessel being inspected. This absorbance magnitude can be compared to a threshold absorbance value which, if exceeded, would indicate the presence of a significant concentration of suspended particulates for a clear walled vessel.

As a second check, the single wavelength reflectance can be measured at 920 or 1050 nm, and compared to a threshold value which, if exceeded, would indicate a substantial concentration of particulates in the liquid. For liquids with high particulate levels, the combined inspection system can then conduct a final inspection of the vessel using the differential wavelength reflectance method. For liquids with low particulate levels, the differential wavelength transmission method can be used for the final inspection.

For the purpose of detecting hazardous liquids inside vessels capable of transmitting IR light, it is also of interest for security purposes to be able to detect the presence of smaller vessels (such as glass or plastic vials or bottles, or plastic bags) that are filled with a potentially hazardous liquid and concealed within a larger vessel capable of transmitting IR light, where the larger vessel is filled with a different liquid such as a water-based liquid. Since many soft drinks are colored, bottles of these colored soft drinks could be used to conceal the presence of a smaller vessel containing a different and potentially hazardous liquid that is contained within the larger bottle of the harmless soft drink. When small vessels of an organic liquid or other hazardous liquid are concealed inside of a larger bottle of harmless water based liquid, the liquid in the smaller bottle will still have a substantially different near-infrared absorption spectrum than the harmless water based liquids.

In a further preferred embodiment of the present invention, for detecting the presence of smaller vessels (including glass or plastic vials or bottles, or plastic bags) that are filled with a potentially hazardous liquid, and concealed within a larger vessel that is filled with a different liquid (such as a water-based liquid), where the larger vessel is capable of transmitting IR light, either the single wavelength or differential wavelength near-infrared imaging technique is employed.

In particular, to detect the above-mentioned spectral differences between the two liquids, near-infrared single wavelength and differential wavelength images are measured at the appropriate wavelength or wavelengths within the 850-1700 nm range, to allow detection through selective imaging of portions of a vessel that contain a different type of liquid than is present in the bulk of the vessel. The presence of a small vessel of an organic liquid concealed within a larger vessel containing a water based liquid can be detected by imaging at a wavelength where the organic liquid has a stronger absorbance than water.

Figure 12:
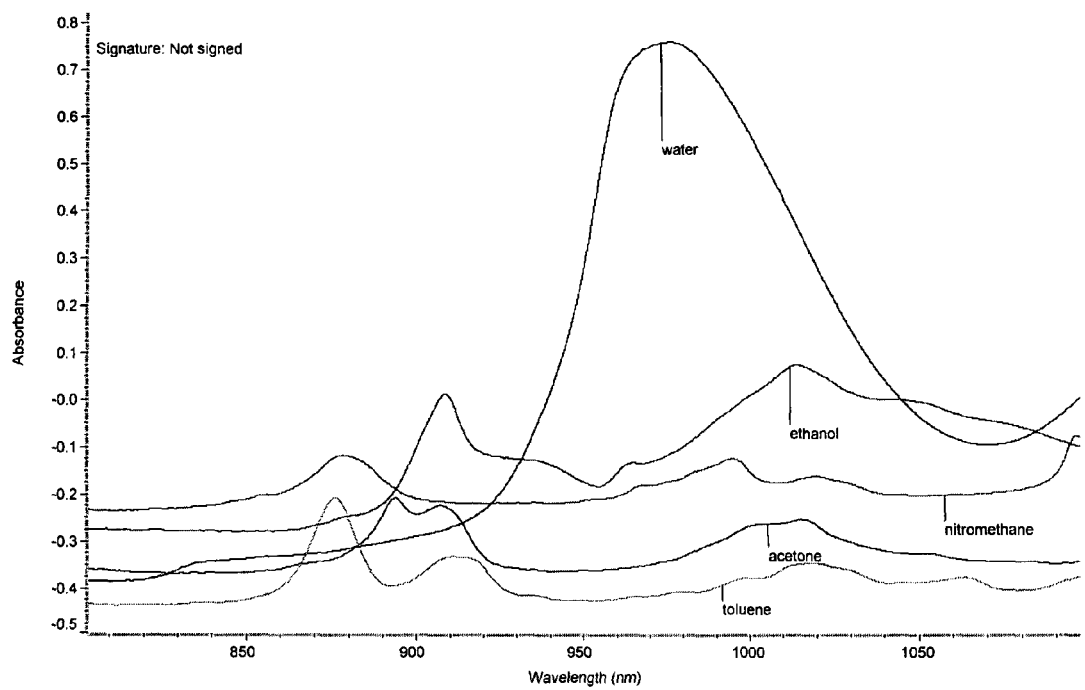
FIG. 12 is a graph illustrating the NIR transmission spectra (in absorbance units vs. nanometers (nm) wavelength units) of water and 4 different organic liquids measured in 61-62 mm diameter glass jars. The spectra demonstrate that water has a much higher absorbance at 980 nm (about 1 absorbance unit higher) than any of the organic liquids, while the absorbance at 920 or 1050 nm are similar between the 5 liquids (absorbance equal within about 0.25 absorbance units at 920 nm).

As illustrated in the near-infrared spectra of FIG. 12, such wavelengths occur in the range of 850-930 nm, as well as 1040-1100 nm. Small vessels containing inorganic liquids, such as a concentrated solution (30-50% by weight) of hydrogen peroxide in water, that are concealed within a larger vessel containing a water-based liquid, can also be detected by the near-infrared transmission or reflection imaging approach using either single or differential wavelength imaging. The wavelengths used for this imaging detection of hydrogen peroxide solutions must include one wavelength where the absorbance for the dissolved hydrogen peroxide is higher than that of pure water.

In a further preferred embodiment of the present invention, the present invention provides a system and method for the simultaneous inspection of a group of 2 or more vessels at once for the presence of a hazardous liquid in one or more of the vessels, (such as a case of 28 bottles of water). In such an embodiment, as illustrated in FIG. 19, the NIR light source (the transmission tungsten halogen lamp) is disposed below the group of vessels, and the NIR imaging means (camera) is located above the group of vessels. During inspection, the path of the light going through the vessels enters each vessel from the bottom thereof, and exits the vessels through the top thereof, such that the light path avoids going through multiple labels on the vessels (labels are normally present on the sides of bottles and not on the top or bottom of a bottle or other container).

The present invention is illustrated by way of the following examples which are not intended to, in any way, limit the scope of the present invention.

Example 1

Test Results Demonstrating Single Wavelength Near-Infrared (NIR) Image Screening of Liquids in Bottles for Hazardous Liquids Vs. Soft Drinks in Plastic Bottles A set of test images of plastic and glass bottles containing water and organic based liquids were recorded both in the visible wavelength range and in the NIR at 980 nm with a consumer video camera operating in the digital camera mode. The camera (Sony® HCR-360 camcorder) has a Si-CCD array detector and has a high gain NIR "nightshot" mode where the camera can see near-infrared light in the 700 to 1000 nm range. The NIR images were measured through a 980 nm center wavelength interference filter with a 10 nm bandpass which was mounted just in front of the camera lens. The NIR images used in this example did not receive any correction with dark or with illumination source background images.

Figure 7:
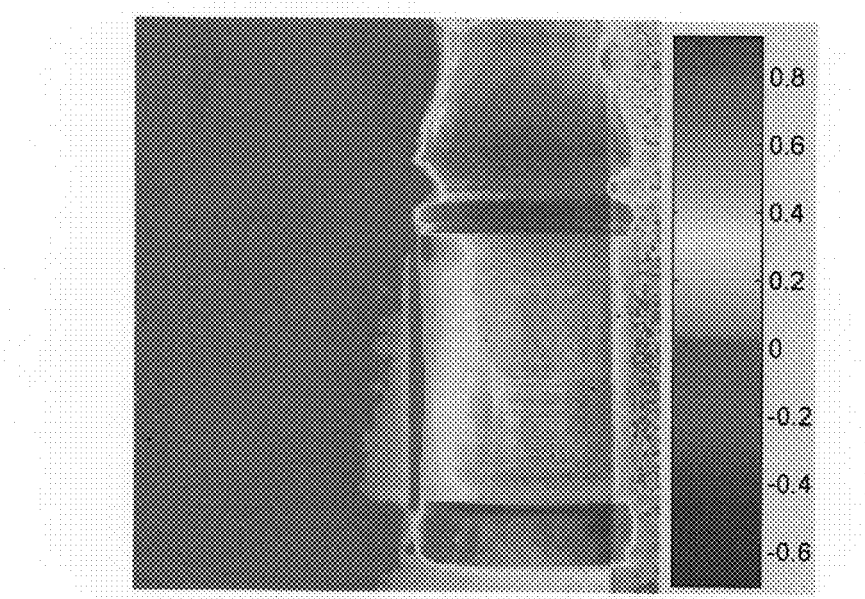
FIG. 7 is a photograph showing a NIR differential wavelength transmission (in ABS units) image of kerosone (left bottle) and cranberry juice (right bottle) measured between 980 nm and 1050 nm (1050 nm image subtracted from 980 nm image), illustrating reduced interference from the plastic labels on the two bottles (with false color intensity scale given on right).

The test images shown in FIGS. 5-7 demonstrate that flammable organic liquids like gasoline, kerosene and nitromethane (a liquid explosive), can be distinguished from water-based liquids using single wavelength band imaging at 975-985 nm. In these imaging tests, the liquids were all contained in PETE plastic bottles with volumes in the 15-19 ounce range, except for the nitromethane and a control water sample which were contained in glass jars with a volume of 200 ml.

The flammable liquids that were tested included: isopropanol, ethanol (95%), gasoline, and kerosene. The soft drinks included: spring water, apple juice, lemonade, white grape juice, and Sprite soda. The organic-based liquids have much lower absorbance at 980 nm than the water-based soft drinks, and the lower absorbance produces a much lighter transmission image than the high absorbance images of the water based soft drinks.

Example 2

Additional measurements were conducted with a NIR hyperspectral imaging system (Spectral Dimensions™

Matrix-NIR), and also with a single point near-infrared Fourier-transform spectrometer (for nitromethane and water only) to measure the absorbance at 980 nm for several water-based soft drinks (including spring water) and also several flammable liquids, including nitromethane.

The hyperspectral imaging system employed a InGaAs diode array camera together with an electronically tunable liquid crystal narrow bandpass filter with a 6 nm bandpass. The tunable filter was set at 980 nm for these absorbance measurements. Using the hyperspectral imaging system, the absorbance and standard deviation were calculated for the 10 image points from each bottle tested. The absorbance results are given in Table 1 below, and show that the absorbance through the water based liquids was consistently higher than that through the organic liquids by about a factor of 6. The absorbance measurement at 980 nm for nitromethane was taken with the Fourier-transform NIR spectrometer.

TABLE 1

Average absorbance and standard deviation of drinks and liquids in plastic bottles at 980 nm (pathlength correction involves dividing the average absorbance by [bottle diameter (mm)/62])

| Drinks and Liquids in Plastic Bottles | Average Absorbance ± Standard Deviation | Bottle Diameter, mm | Pathlength Corrected Average Absorbance ± Standard Deviation |
|---|---|---|---|
| Apple Juice | 1.263 ± 0.154 | 67 | 1.169 ± 0.143 |
| Lemonade | 1.433 ± 0.112 | 72 | 1.234 ± 0.096 |
| Water | 1.137 ± 0.125 | 62 | 1.137 ± 0.125 |
| Sprite | 1.312 ± 0.110 | 72 | 1.130 ± 0.095 |
| Isopropanol | 0.223 ± 0.041 | 64 | 0.216 ± 0.040 |
| Ethanol | 0.311 ± 0.046 | 64 | 0.301 ± 0.045 |
| Gasoline | 0.139 ± 0.061 | 72 | 0.120 ± 0.053 |
| Kerosene | 0.137 ± 0.080 | 72 | 0.118 ± 0.069 |
| Nitromethane | 0.18 | 62 | .18 |

Example 3

Two Wavelength Differential Wavelength Transmission Imaging of Softdrink Bottles Showing Reduced Interference from Bottle Labels and Cardboard Container Walls Additional NIR transmission imaging measurements of the same plastic bottles of cranberry juice and kerosene shown in FIG. 4 were measured with the NIR hyperspectral imaging system described above at both 980 and 1050 nm, using the tunable 6 nm bandwidth liquid crystal narrow bandpass filter to select the wavelength bands. The images at 980 and 1050 nm were converted to absorbance and then subtracted (980 nm ABS image minus 1050 nm ABS image) using image processing software to produce a differential wavelength image.

Figure 8:
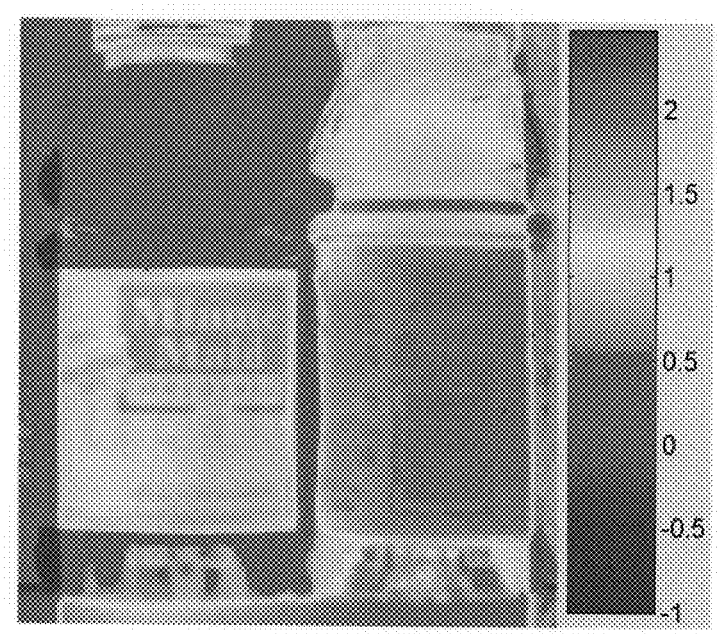
FIG. 8 is a photograph showing a single wavelength transmission image at 980 nm (in ABS units) of the same bottles of kerosone (left bottle) and cranberry juice (right bottle) illustrated in FIGS. 4(a), 4(b) and 7, showing a greater level of visibility and interference from the bottle labels relative to the differential wavelength image in FIG. 7.

In FIG. 7 and FIG. 8, the differences between a single wavelength image (in ABS units) at 980 nm can be compared with the differential wavelength image measured between 980 and 1050 nm for the bottles of cranberry juice and kerosene. The images in FIG. 7 and FIG. 8 demonstrate that the differential wavelength image greatly reduces the interference from the labels on the two bottles (see FIG. 4(a) for a visible wavelength image of these two bottles with the same labels) relative to the single wavelength image at 980 nm (single wavelength image also measured with the same hyperspectral imaging system).

Figure 9:
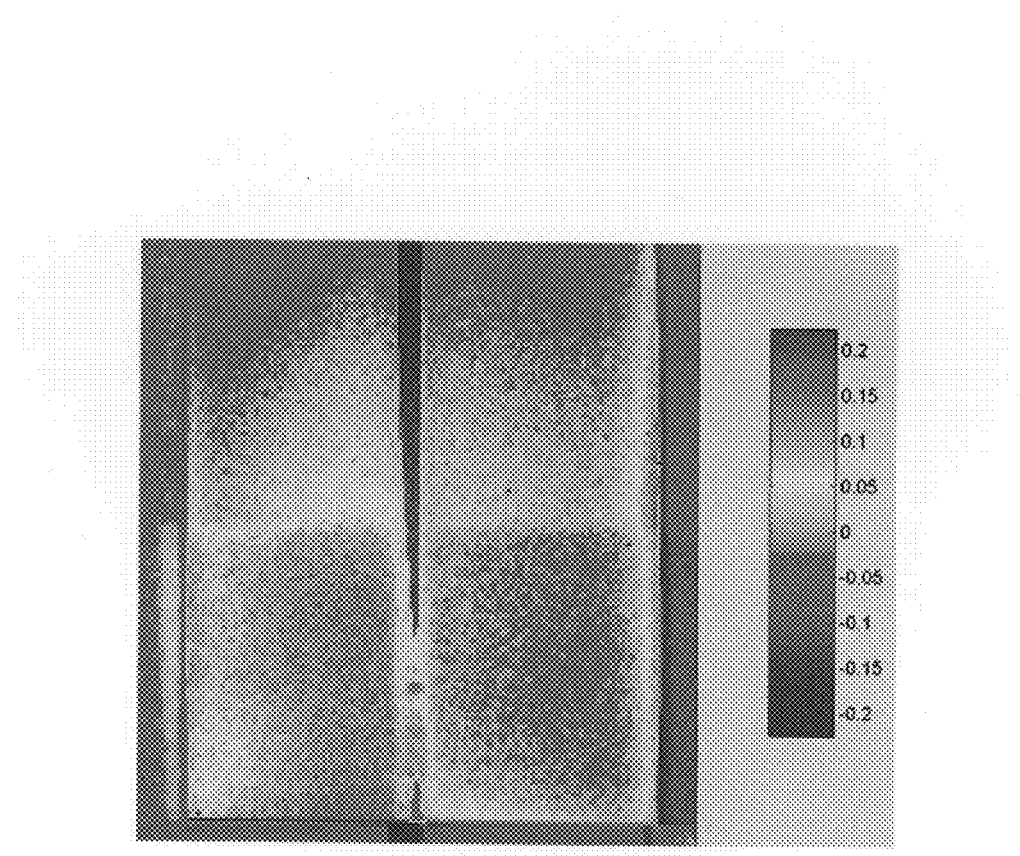
FIG. 9 is a photograph showing a NIR differential wavelength transmission image of water (left box) and ethanol (right box) in 32 oz cardboard orange juice containers measured between at 980 nm and 1050 nm.

The image shown in FIG. 9 shows a NIR differential wavelength transmission image measured between 980 and 1050 nm for two cardboard orange juice containers, with one container holding water and the other holding denatured ethanol. The image shown in FIG. 9 was measured using the NIR hyperspectral imaging system. The image shown in FIG. 9 exhibits substantial contrast between the water and ethanol, while a single wavelength image (not shown here) would show very little difference in absorbance between the water and alcohol because of the light scattering and absorbance interference from the cardboard container walls.

Example 4

NIR reflectance imaging was tested for its ability to differentiate water based liquids from organic liquids when the liquids contain substantial amounts of suspended particles that make the liquids opaque as a result of light scattering effects. A 900-1700 nm NIR hyperspectral imaging system (MatrixNIR™, from Spectral Dimensions™) was used to measure differential wavelength reflection images which involve subtraction of an image (in −log(reflectance) units) at one wavelength from an image at a second wavelength.

The samples measured included Similac® baby formula contained in a 40 ml glass vial and in a plastic baby bottle, white Teflon® powder suspended in safflower oil in a 40 ml glass vial, and gasoline with Teflon® powder and Ajax® dish washing detergent plus water added in a 125 ml plastic bottle. The safflower oil and gasoline samples with the Teflon® powder were prepared by stirring for 30 minutes with a magnetic stirrer at room temperature. The final mixture for the safflower oil and gasoline plus Teflon® powder is a milky suspension similar in appearance to baby formula.

The gasoline-water-Teflon® powder suspension was prepared by mixing gasoline and water (95 parts/5 parts by weight) first, and then adding Teflon® powder and Ajax® dish liquid, and stirring for 30 minutes at room temperature, which gave a final suspension mixture with light yellow color. The reflectance images were measured with the same geometry shown in FIG. 3, where the light source and the camera are both on the same side of the bottles being inspected.

Figure 10A:
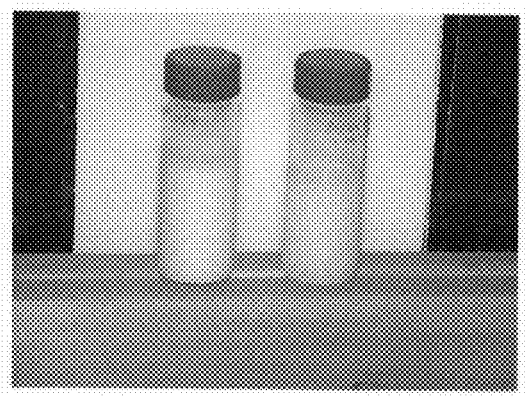
FIG. 10(a) is a photograph showing a visible wavelength reflection image of baby formula (left glass bottle) and safflower oil with micro-fine Teflon powder suspended therein (right side glass bottle).
Figure 10B:
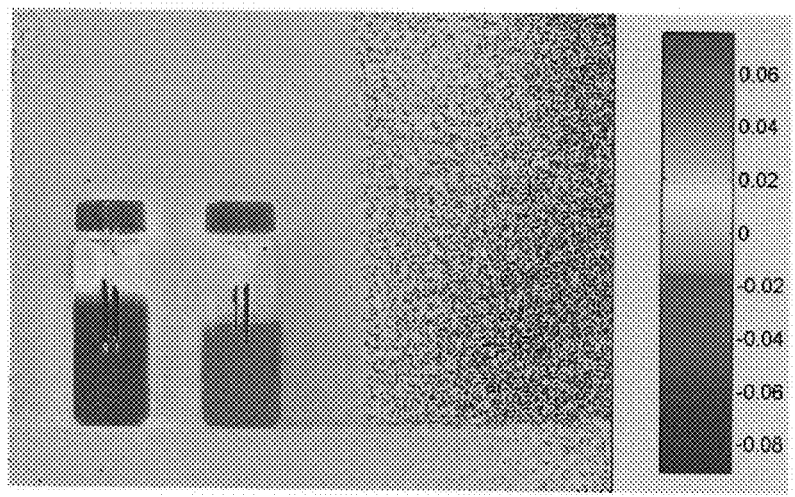
FIG. 10(b) is a photograph showing a near-infrared differential wavelength reflection image (in −log(reflectance) units, with false color intensity scale given on right) of the same bottles of baby formula (left) and safflower oil (right) with suspended Teflon particles measured between 980 and 1050 nm. The differential NIR image shows that the baby formula has a positive value of −log(reflectance) of about 0.07, while the safflower oil with suspended particles has a negative −log(reflectance) value of about −0.03.
Figure 11A:
FIG. 11(a) is a photograph showing a visible wavelength reflection image of baby formula (left) in a clear plastic baby bottle and gasoline (right) with fine Teflon powder and Ajax dish washing liquid detergent added thereto in a PETE plastic bottle.
Figure 11B:
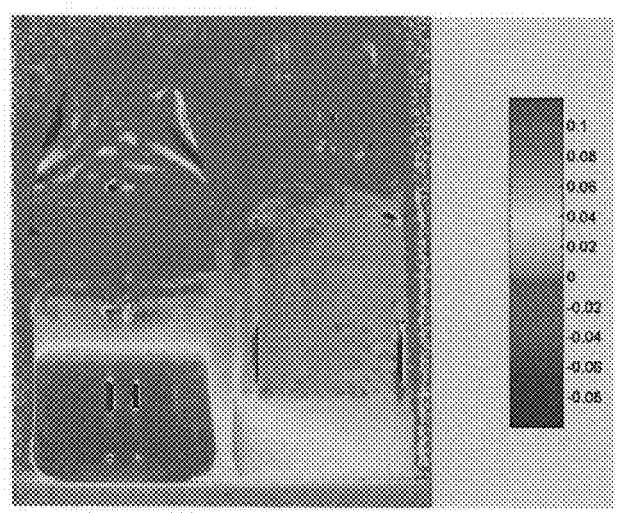
FIG. 11(b) is a photograph showing a differential wavelength reflection NIR image measured between 980 and 1050 nm (in −log(reflectance) units, with false color intensity scale given on right) of baby formula (left) and gasoline (right) with Teflon powder, water, and Ajax dish detergent added thereto. The differential wavelength NIR image of the baby formula shows a −log(reflectance) value of about 0.11 while the image of the gasoline with suspended particles has a −log(reflectance) of about 0.035 that is significantly lower.

The differential wavelength reflectance imaging results are given in FIG. 10 and FIG. 11. To obtain the differential images, the image (in −log(reflectance) units) at 1050 nm was subtracted from the image at 980 nm. FIG. 10 shows a visible wavelength reflection image followed by a NIR differential wavelength image of two 40 ml glass bottles standing next to each other with one containing baby formula and the other containing a suspension of Teflon® powder in safflower oil.

FIG. 11 shows a visible wavelength image followed by a NIR differential wavelength image of two plastic bottles standing next to each other with one bottle containing baby formula and the other bottle containing a gasoline-water-Teflon® powder suspension.

The results show that in both pairs of bottles, the water based particle suspension (baby formula) cannot be easily distinguished from the organic liquid based particle suspension using the visible wavelength reflection image. In the differential wavelength NIR reflection images, the water based and organic liquids can easily be distinguished from each other as a result of the substantial differences in the −log(reflectance) values between the two liquids.

Example 5

Figure 22:
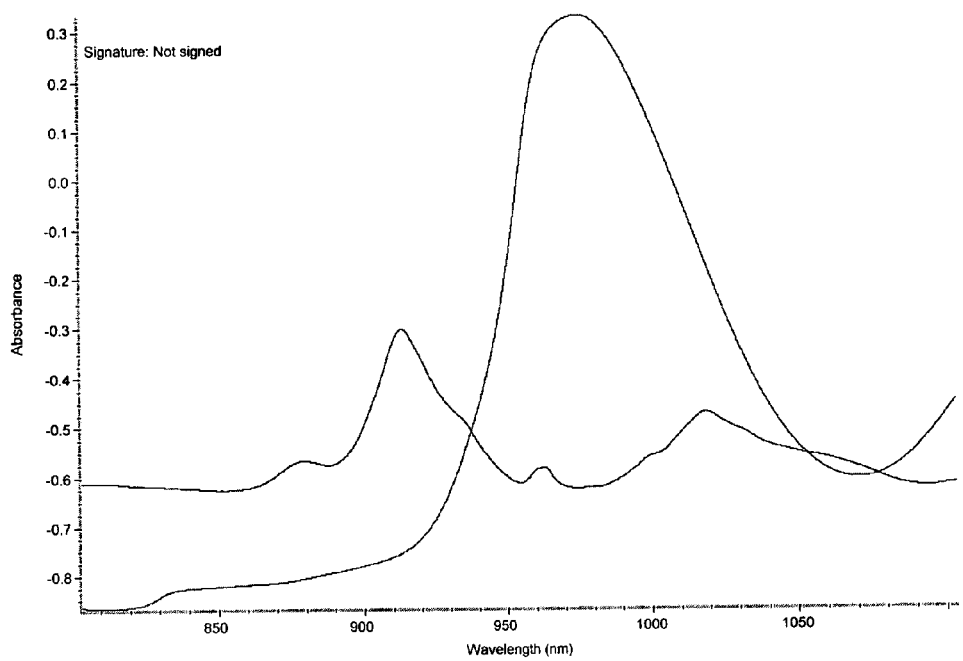
FIG. 22 is a graph of the FT-NIR transmission spectra of water (curve with one strong peak at 980 nm) and gasoline (curve with smaller peaks at 923 and 1020 nm) in 16 oz. PETE bottles with similar bottle diameters (bottle diameters about 60 mm). These spectra illustrate a strong peak at 980 nm for water, where gasoline has very weak absorption.

Additional NIR Transmission Spectra of Water and Several Organic Liquids Demonstrating Much Higher Absorbance for Water A series of transmission spectra (in absorbance units) in the 800-1200 nm NIR spectral range were measured for water and 4 different organic liquids contained in glass jars with a diameter of 61-62 mm. The 4 organic liquids measured were ethanol, toluene, nitromethane, and acetone. These spectra are shown in FIG. 12. The difference between the NIR transmission spectra of water and gasoline was similar and is shown in FIG. 22.

The spectra demonstrate that the absorbance for water at 980 nm is much higher than that of any of the 4 organic liquids, which cover a wide variety of organic compound types. The spectra in FIG. 12 also show that the absorbance of the 4 organic liquids is very similar to that of water at wavelengths just off of the 980 water absorption band such as 920 nm and 1050 nm. The large absorbance difference at 980 nm and the small differences at 920 or 1050 nm provides the basis for differentiating water based from organic liquids using differential wavelength imaging.

Example 6

NIR Imaging of Hazardous Liquids Contained in Vials Concealed in a Bottle of Orange Gatorade®

Three liquids contained in 20 or 40 ml glass vials were concealed inside of a 20 oz. bottle of orange Gatorade®, and were detected by using NIR transmission imaging. The Gatorade® bottle was made of PETE plastic. Both single wavelength and differential wavelength imaging was employed. The images were measured in the transmission mode using a Spectral Dimensions® near-infrared hyperspectral imaging system, which employs an InGaAs camera and a liquid crystal tunable narrow bandpass filter for wavelength selection. The three test liquids contained in the glass vials that were concealed in the Gatorade® bottle contained the following:

(1) 50% concentration hydrogen peroxide;
(2) Acetone (with orange dye added thereto); and
(3) Water.

Figure 13:
FIG. 13 is a near-infrared image, measured at a wavelength of 1022 nm, of a bottle of orange Gatorade® with a concealed 40 ml glass vial containing concentrated (50%) hydrogen peroxide in water.

FIG. 13 illustrates the results of imaging a concealed glass vial of 50% hydrogen peroxide at a single wavelength. The image shown in FIG. 13 was measured at 1022 nm with the hydrogen peroxide vial close to the camera side of the Gatorade® bottle. The hydrogen peroxide vial can be identified in the image, and appears as the darker red-orange colored area.

Figure 14:
FIG. 14 is a visible wavelength image of the bottle of Gatorade® with the concealed vial of hydrogen peroxide shown in FIG. 13.

FIG. 14 illustrates a visible wavelength image of the same vial of hydrogen peroxide inside of the Gatorade®, with the vial close to the front of the Gatorade® bottle. FIG. 14 shows that the hydrogen peroxide vial is well concealed by the Gatorade® when viewed at visible wavelengths, with only the dark green vial cap being visible. A clear vial cap would permit complete concealment of the vial with respect to visible light inspection.

Figure 15:
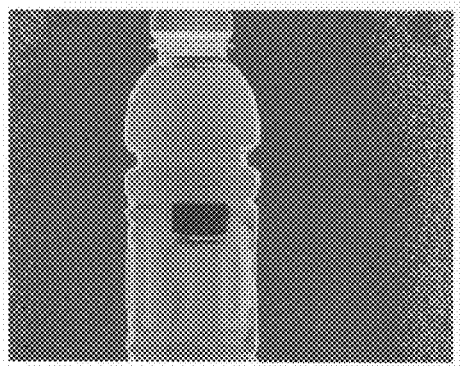
FIG. 15 is a near-infrared image measured at 1022 nm of the bottle of Gatorade® shown in FIG. 13, with a 40 ml vial of pure water contained therein, demonstrating that the wavelength of 1022 nm is effective for imaging hydrogen peroxide, but not effective for imaging pure water.
Figure 16:
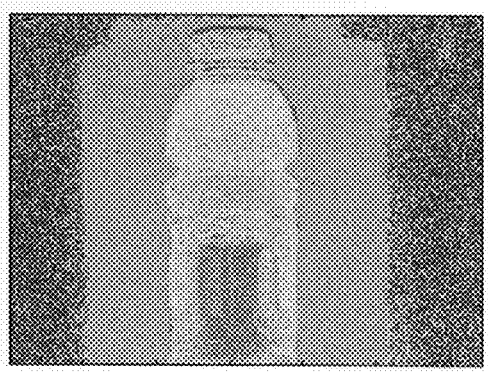
FIG. 16 is a differential wavelength near-infrared image, measured between 1052 and 1082 nm, (image at 1052 nm minus the image at 1082 nm), of the same concealed vial of hydrogen peroxide contained inside of the bottle of Gatorade® shown in FIG. 13. As illustrated, this differential wavelength image shows better contrast for the vial of hydrogen peroxide than the single wavelength image shown in FIG. 13.

As illustrated in FIG. 15, a control vial of pure water that was imaged inside the Gatorade® (close to the front of the bottle) at the same wavelength (1022 nm) used for the hydrogen peroxide, cannot be easily seen. FIG. 15 demonstrates that imaging at 1022 nm is chemically selective for hydrogen peroxide vs. water. Differential wavelength NIR imaging between 1052 and 1082 nm, gives better image contrast, as shown in FIG. 16, for the vial of 50% hydrogen peroxide concealed in the Gatorade.

Figure 17:
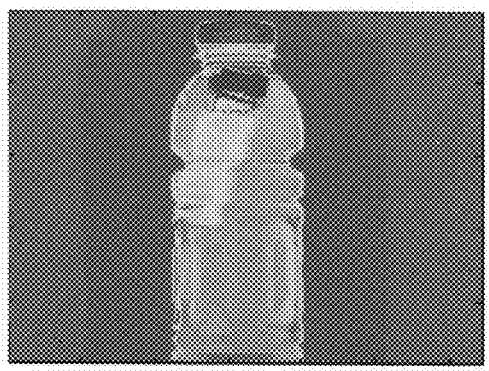
FIG. 17 is single wavelength near-infrared image measured at 1058 nm of a 40 ml vial of acetone (with a small amount of orange dye added) that is concealed in the orange Gatorade® bottle.
Figure 18:
FIG. 18 is a visible wavelength image of the bottle of Gatorade® with the concealed vial of acetone shown in FIG. 17.

The single wavelength NIR image measured for a vial of acetone containing a small amount (less than 0.001%) of orange dye (chlorophenol red) added to match the Gatorade® color, that is concealed inside the Gatorade® bottle, is shown in FIG. 17. A visible wavelength image of the same vial of acetone in the Gatorade® bottle is illustrated in FIG. 18, which shows again that the vial is well concealed with respect to visual inspection with the human eye, except for the vial cap.

Example 7

Figure 20:
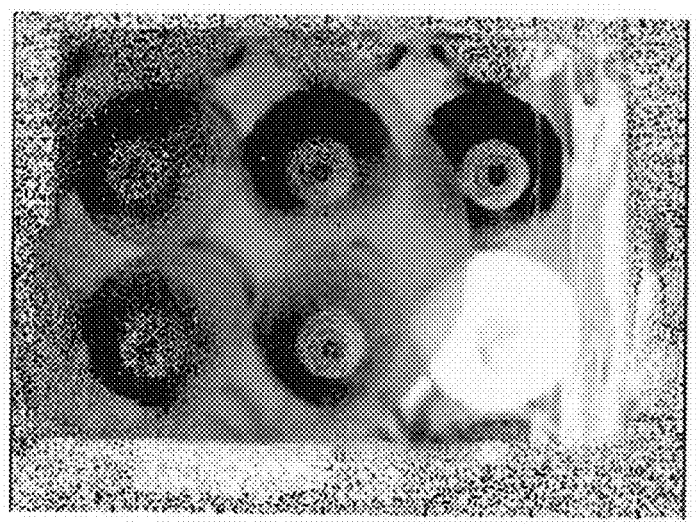
FIG. 20 is a NIR differential wavelength transmission image (between 980 and 1050 nm) of a portion of a case of 28 700 ml bottles of spring water, where one bottle (the white bottle in lower right) contains isopropanol instead of water. The case packaging consists of a corrugated cardboard bottom with shrink wrap over everything. There are some printed graphics on the top of the shrink wrap. The portion of the case of bottles imaged here was illuminated from below the case as shown in FIG. 19.

As illustrated in FIG. 20, a portion of a case of spring water bottles was imaged using a near-infrared spectral imaging system consisting of a NIR camera together with a liquid crystal tunable narrow bandpass filter. The system used for imaging was very similar to that shown in FIG. 2, except that the camera had a liquid crystal tunable filter instead of a filter wheel to select the two imaging wavelength bands used for the differential wavelength image.

Figure 21:
FIG. 21 is a visible wavelength image of a portion of the case of 28 700 ml bottles of spring water shown in FIG. 20, with the dotted square showing the area covered in FIG. 20 with the near-infrared camera image. As illustrated, in the visible range, there is no visible difference between the bottle containing isopropanol and the bottles containing spring water.

In particular, as shown in FIG. 21, a visible image of the portion of the case of spring water bottles was taken. Then, a NIR differential wavelength transmission image (between 980 and 1050 nm) of a portion of the case of 28 bottles of spring water bottles (700 ml size) was taken. The NIR differential wavelength transmission image clearly identifies the one bottle (white bottle in lower right) containing isopropanol instead of water.

This example illustrates that the system and method of the present invention can be utilized for, and is efficient at, inspecting cartons/cases of vessels, such as bottles and other paper containers capable of transmitting NIR light. Although the case packaging consists of a corrugated cardboard bottom with shrink wrap over everything, the bottle containing isopropanol was clearly identifiable. Further, even though there is some printed graphics on the top of the shrink wrap, by disposing the NIR light source underneath of the case of containers, the system and method were able to efficiently inspect the containers, by avoiding extreme interference by the labels.

The advantages of the present invention relative to other conventional approaches are:
(1) lower cost;
(2) higher analysis speed;
(3) higher selectivity and specificity for differentiating water vs. organic based liquids;
(4) the ability to accommodate irregular container shapes including those with sections of or all of the container walls having a small radius of curvature; and
(5) the ability to perform the container inspection without contacting the container.
(6) the ability to detect, through the imaging aspects of the invention, the presence of smaller bottles or containers of organic based liquids that are concealed in a water-based liquid contained inside of a larger bottle or container.

Although specific embodiments of the present invention have been disclosed herein, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

LIST OF DRAWING ELEMENTS

1: NIR digital or video camera
2: computer processing means
3: narrow bandpass optical interference filter
4: vessel (such as a bottle or container) that is being inspected
5: NIR light sources (two sources shown)
6: diffuser plate 7: optical shutter
8: optical wavelength selecting means

What is claimed is:

1. A system for non-invasively inspecting vessels comprising:
   (a) a near-infrared (NIR) imaging means comprised of a detector array and one or more lenses disposed adjacent thereto for taking an NIR image of the vessels;
   (b) one or more NIR light sources disposed opposite the NIR imaging means for illuminating the vessels;
   (c) one or more diffuser plates disposed adjacent the one or more NIR light sources;
   (d) an optical wavelength selecting means capable selecting a wavelength to be transmitted therethrough, said optical wavelength selecting means being disposed between the one or more lenses and the vessels, between the detector array and the one or more lenses, or between the one or more light sources and the vessels;
   (e) a computer processing means in communication with the NIR imaging means; and
   (f) a computer readable database in communication with the computer processing means, said computer readable database comprising absorbance IR spectroscopic data corresponding to water based and organic based liquids.

2. The system for non-invasively inspection vessels of claim 1, wherein the computer readable database further comprises IR spectroscopic data for known explosive compositions in the range of 700 nm to 1600 nm.

3. The system for non-invasively inspecting vessels of claim 1, further comprising:
   (g) a computer readable medium including computer instructions for correlating measured peak absorbances to the IR spectroscopic data of the known explosive compositions, the computer instructions including instructions for:
   determining the wavelength(s) of IR light to be used in the inspection of the vessels;
   instituting the inspection of the vessel, comprising controlling operation of the NIR light sources and the NIR imaging means, so as to collect spectroscopic test data;
   transmitting of the spectroscopic test data to the computer processing means;
   querying the computer readable database, so as to compare the collected spectroscopic test data to the IR spectroscopic data of known explosive compositions;
   determining which known explosive composition(s) correspond to the collected spectroscopic test data; and
   producing a user report comprising data concerning the known explosive composition(s) corresponding to the collected spectroscopic test data.

4. The system for non-invasively inspecting vessels of claim 3, wherein the optical wavelength selecting means is a computer controlled, electrically tunable filter.

5. The system for non-invasively inspecting vessels of claim 1, wherein the one or more NIR light sources are in communication with the computer processing means.

6. The system for non-invasively inspecting vessels of claim 1, wherein the optical wavelength selecting means comprises one or more narrow bandpass optical interference filters having a center wavelength corresponding to a peak absorbance of water in the NIR range.

7. The system for non-invasively inspecting vessels of claim 6, wherein the optical wavelength selecting means further comprises and one or more narrow bandpass optical interference filters having a center wavelength corresponding to specific selective wavelengths corresponding to primary IR absorption peaks of known explosives.

8. The system for non-invasively inspecting vessels of claim 6, wherein the optical wavelength selecting means comprises a plurality of movable narrow bandpass optical filters, such that the position of the filters, relative to input aperture of the NIR imaging means, may be controlled via the computer processing means.

* * * * *